(12) United States Patent
Harkema et al.

(10) Patent No.: US 11,691,016 B2
(45) Date of Patent: Jul. 4, 2023

(54) METHODS FOR NEUROSTIMULATOR PULSE OVERLAP CONTROL

(71) Applicant: University of Louisville Research Foundation, Inc., Louisville, KY (US)

(72) Inventors: Susan J. Harkema, Louisville, KY (US); Yangsheng Chen, Louisville, KY (US); Claudia Angeli, Louisville, KY (US); Douglas J. Jackson, New Albany, IN (US); Manikandan Ravi, Louisville, KS (US); John Naber, Goshen, KY (US); Robert S. Keynton, Louisville, KY (US); Thomas Roussel, Louisville, KY (US); Saliya Kirigeeganage, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 138 days.

(21) Appl. No.: 17/048,955

(22) PCT Filed: Apr. 19, 2019

(86) PCT No.: PCT/US2019/028225
§ 371 (c)(1),
(2) Date: Oct. 19, 2020

(87) PCT Pub. No.: WO2019/204677
PCT Pub. Date: Oct. 24, 2019

(65) Prior Publication Data
US 2021/0228884 A1 Jul. 29, 2021

Related U.S. Application Data

(60) Provisional application No. 62/660,304, filed on Apr. 20, 2018.

(51) Int. Cl.
*A61N 1/36* (2006.01)

(52) U.S. Cl.
CPC ..... *A61N 1/36175* (2013.01); *A61N 1/36062* (2017.08)

(58) Field of Classification Search
CPC ............ A61N 1/36175; A61N 1/36062; A61N 1/36146; A61N 1/3616
See application file for complete search history.

(56) References Cited

U.S. PATENT DOCUMENTS

2004/0133248 A1* 7/2004 Frei ..................... A61N 1/36146
607/45
2011/0125217 A1* 5/2011 Carter ................ A61N 1/36038
607/56

(Continued)

OTHER PUBLICATIONS

An Introduction to Sampling Theory, Digital Signal Processing: Principles, Algorithms, and Applications, by J. Proakis and D. Manolakis, New York: Macmillan Publishing Company, 1992, by Thomas Zawistowski & Paras Shah (Year: 1992).*

(Continued)

*Primary Examiner* — Paula J Stice
(74) *Attorney, Agent, or Firm* — Dentons Bingham Greenebaum LLP; Brian W. Chellgren

(57) ABSTRACT

Patients with spinal cord injuries have benefited from neurostimulation therapy comprising delivery of electrical stimulation to enable or excite neurological responses using an implantable neurostimulator having an electrode array. Dangerous levels of charge are avoided while providing multiple, simultaneous stimulation waveforms by inducing a short in an electrode when a monitored value reaches or exceeds a predetermined threshold.

17 Claims, 3 Drawing Sheets

(56) References Cited

U.S. PATENT DOCUMENTS

2011/0313488 A1* 12/2011 Hincapie Ordonez ......................
                                                    A61N 1/36146
                                                            607/59
2012/0290040 A1* 11/2012 Moffitt ............... A61N 1/37241
                                                            607/45
2016/0346530 A1   12/2016 Jeffrey et al.
2018/0015266 A1    1/2018 Amery
2018/0015286 A1*   1/2018 Liedler .............. A61N 1/36175

OTHER PUBLICATIONS

Extended European Search Report for EP 19 78 9118, dated Jan. 17, 2022. Applicant: University of Louisville Research Foundation, Inc.
D. R. Merrill, M. Bikson and J. G. R. Jefferys, "Electrical stimulation of excitable tissue: design of efficacious and safe protocols," Journal of neuroscience methods, vol. 141, pp. 171-198, 2005.
D. B. McCreery, W. F. Agnew, T. G. H. Yuen and L. Bullara, "Charge density and charge per phase as cofactors in neural injury induced by electrical stimulation," IEEE transactions on biomedical engineering, vol. 37, pp. 996-1001, 1990.
A. W. F., M. D. B., Y. T. G. and B. L. A., "Histologic and physiologic evaluation of electrically stimulated peripheral nerve: considerations for the selection of parameters," Annals of Biomedical Engineering, vol. 17, No. 1, pp. 39-60, 1981.
International Search Report and Written Opinion for PCT/US 19/28225, Mailed Jul. 12, 2019, Applicant: University of Louisville Research Foundation.

* cited by examiner

METHODS FOR NEUROSTIMULATOR PULSE OVERLAP CONTROL

This application claims the benefit of U.S. provisional patent application Ser. No. 62/660,304, filed 20 Apr. 2018, for METHODS FOR NEUROSTIMULATOR PULSE OVERLAP CONTROL, incorporated herein by reference.

FIELD OF THE INVENTION

Patients with spinal cord injuries have benefited from neurostimulation therapy comprising delivery of electrical stimulation to enable or excite neurological responses using an implantable neurostimulator having an electrode array. Dangerous levels of charge are avoided while providing multiple, simultaneous stimulation waveforms by inducing a short in an electrode when a monitored value reaches or exceeds a predetermined threshold.

BACKGROUND

Serious spinal cord injuries (SCI) result in partial (incomplete) or substantially complete loss of sensory motor function below the level of the spinal lesion. For individuals with incomplete loss of motor function, substantial recovery of standing and stepping recovery has been demonstrated through the application of task specific physical rehabilitation training. Recently, task specific physical rehabilitation training has been combined with epidural stimulation (ES) of the spinal cord in patients with incomplete and complete motor paralysis. High density epidural stimulating electrode arrays can provide spatially selective stimulation to regions of the spinal cord to facilitate muscle movement.

SCI and other conditions may benefit from the delivery of stimulus intended to enable or excite multiple neurological responses using an implantable neurostimulator. A targeted neurological function, such as blood pressure, may respond to a particular electrical stimulus or waveform at a specific location, amplitude, frequency, pulse width or a combination thereof. Other functions, such as muscle flexon, may require a different waveform to produce the desired response. For situations where multiple neurological functions need to be stimulated at the same time, the differing stimulus signals may interfere and create challenges in maintaining the charge balance of electrodes during stimulation.

The circuit shown in FIG. 1 is a simplified exemplary model of four electrodes being stimulated using two different waveforms for neurostimulation. A first waveform connects to electrode pair 4 and 3, while a second waveform connects to electrode pair 2 and 1. Node R is common to all electrodes, since all electrodes are in a common conductive medium, e.g., tissue and fluid. Interactions between each pair of electrode sets or waveforms can occur when electrodes are not isolated from connecting circuits. These coupled interactions between waveforms with overlapping pulses can add constructively or destructively to each other, depending upon if each pulse is in the charging or discharging phase. Moreover, overlapping pulses from multiple and simultaneous waveforms may result in undesired stimuli and could result in larger than intended and potentially dangerous stimuli from constructive interference in scenarios where the overlapping pulses add together. Overlapping pulses can make charge balancing very complicated, as a clinician may not know the exact behavior of interactions between pulses. This scenario of overlapping pulses may occur routinely if each waveform is allowed to independently vary in frequency and pulse width.

The common approach in the industry for managing interaction between waveforms is to not allow overlap of stimulus pulses between electrode pairs or sets, typically by blanking or shifting pulses to avoid overlaps. One approach is to manage interactions between waveforms by detecting waveform overlap, defined as pulses within 3 milliseconds (ms) of each other, and if detected, automatically delaying one of the pulses by 3 ms (i.e., shifting a pulse in time). This approach has several shortcomings, including (1) no user understanding of the effect this pulse delay has on the frequency change of the waveform—the more overlapping pulses are delayed, the greater the effect on the frequency change of the waveform—or even which waveform was affected, (2) no user control or feedback, as the waveform management is performed autonomously by hardware, (3) no pre-processing of the phase relationship between waveforms to minimize the number of overlap occurrences, (4) no option to select the length of the delay or select which of the overlapping pulses receives the delay, (5) no option to "blank" or refrain from emitting the overlapping pulse at a particular instant in time, (6) no ability to prioritize which of the overlapping waveforms will be blanked or phase shifted, (7) no ability to change the recharge width of the pulse, (8) no ability to change the shorting width of the pulse, and (9) no ability to accommodate global shorting windows. Despite the industry approach for managing waveform interactions, the assembly and delivery of sophisticated stimulation patterns while minimizing undesirable interactions between waveforms remains a challenge.

SUMMARY

Disclosed herein are methods for minimizing undesirable interactions between waveforms, particularly in neurostimulation therapy for spinal cord injury. Known methods for minimizing undesirable interactions between multiple independent waveforms include blanking pulses and shifting pulses to avoid overlap. However, blanking or shifting pulses may create undesirable stimulation patterns in a patient. Methods disclosed herein include allowing overlap of stimulus pulses between electrode pairs or sets within a controlled charge range, and hardware-based solutions for monitoring electrode charge levels and shorting electrodes to ground if the charge, charge density or other monitored value reaches or exceeds a predetermined threshold.

This summary is provided to introduce a selection of the concepts that are described in further detail in the detailed description and drawings contained herein. This summary is not intended to identify any primary or essential features of the claimed subject matter. Some or all of the described features may be present in the corresponding independent or dependent claims, but should not be construed to be a limitation unless expressly recited in a particular claim. Each embodiment described herein is not necessarily intended to address every object described herein, and each embodiment does not necessarily include each feature described. Other forms, embodiments, objects, advantages, benefits, features, and aspects of the present invention will become apparent to one of skill in the art from the detailed description and drawings contained herein. Moreover, the various apparatuses and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

A better understanding of the present invention will be had upon reference to the following description in conjunction with the accompanying drawings.

DETAILED DESCRIPTION OF THE PREFERRED EMBODIMENTS

Figure 1:
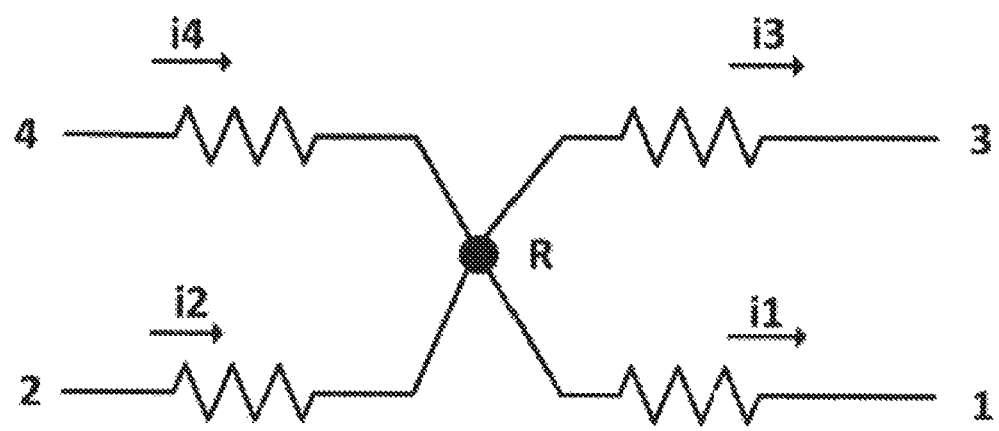
FIG. 1 is a schematic of an exemplary circuit for providing two simultaneous and independent waveforms.

For the purposes of promoting an understanding of the principles of the invention, reference will now be made to selected embodiments illustrated in the drawings and specific language will be used to describe the same. It will nevertheless be understood that no limitation of the scope of the invention is thereby intended; any alterations and further modifications of the described or illustrated embodiments, and any further applications of the principles of the invention as illustrated herein are contemplated as would normally occur to one skilled in the art to which the invention relates. At least one embodiment of the invention is shown in great detail, although it will be apparent to those skilled in the relevant art that some features or some combinations of features may not be shown for the sake of clarity.

Any reference to "invention" within this document is a reference to an embodiment of a family of inventions, with no single embodiment including features that are necessarily included in all embodiments, unless otherwise stated. Furthermore, although there may be references to "advantages" provided by some embodiments of the present invention, other embodiments may not include those same advantages, or may include different advantages. Any advantages described herein are not to be construed as limiting to any of the claims.

Specific quantities (spatial dimensions, dimensionless parameters, etc.) may be used explicitly or implicitly herein, such specific quantities are presented as examples only and are approximate values unless otherwise indicated. Discussions pertaining to specific compositions of matter, if present, are presented as examples only and do not limit the applicability of other compositions of matter, especially other compositions of matter with similar properties, unless otherwise indicated. Unless stated otherwise, explicit approximate quantities (e.g., about 1; about 20) refer to a range of ±5% of the recited quantities (e.g., "about 1" refers to 0.95 to 1.05; "about 20" refers to 19 to 21).

The present invention comprises methods for minimizing undesirable interactions between waveforms, particularly in neurostimulation therapy for spinal cord injury. In neurostimulation therapy, an electrode array comprising a plurality of electrodes disposed on a flexible biocompatible material is provided. Preferably, the electrodes comprise one or more biocompatible metals or alloys, as known in the art. Sets of electrodes within the array generate waveforms, the electrode array being configured to produce at least two simultaneous waveforms, each waveform having a frequency, a pulse width, a phase and at least one pulse.

The electrode array and resulting waveforms may be optimized by controlling hardware or software to allow overlapping pulses between waveforms within a controlled charge range. In some embodiments, waveforms are optimized by shorting the electrodes if the charge or charge density reaches or exceeds a predetermined threshold. The predetermined threshold is preferably selected to short the electrodes before reaching a charge or charge density that may be damaging to the patient, the electrodes, or both. In some embodiments, the predetermined threshold is a charge density of 100 $\mu C/cm^2$. In other embodiments, the predetermined threshold may be one of 80 $\mu C/cm^2$, 90 $\mu C/cm^2$, 110 $\mu C/cm^2$, 120 $\mu C/cm^2$, or higher or lower values depending on the resilience of the electrodes and further research on the resilience of patients.

In some embodiments, each electrode in the electrode array includes a driving circuit including an amplifier and an analog-to-digital converter (ADC), as known in the art, to measure the current (I) through the electrode. The charge (Q) can be calculated by integrating current over time (t): $Q=\int I \cdot dt$. The electrode array is in electrical communication with an implantable pulse generator (IPG) including a microcontroller. The microcontroller calculates the current (I) over time to determine the charge (Q), then calculates the charge density (Q/A) by dividing charge (Q) by the surface area of each electrode (A).

Figure 2:
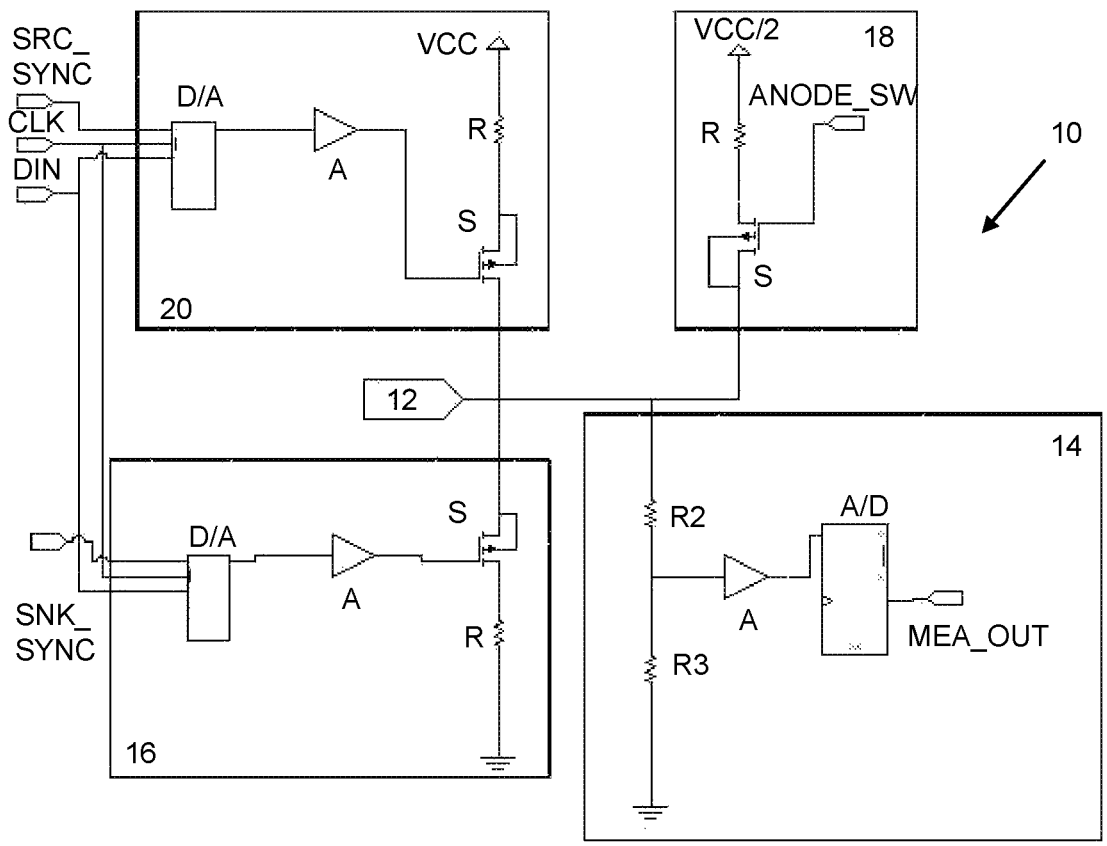
FIG. 2 is a circuit diagram of an exemplary electrode for an implantable pulse generator.

FIG. 2 depicts an exemplary circuit diagram of an IPG constant current stimulator circuit 10. An electrode array would be in electrical communication with an implanted microcontroller with a circuit 10 connected to each electrode in the array. The exemplary stimulator circuit 10 includes an electrode 12, an ADC block 14 (i.e., an analog to digital converter block), a sink block 16 (i.e., a stimulus current control block), an anode block 18 (i.e., the anode switch control block), and a source block 20 (i.e., the active balance current control block). Source block 20 and sink block 16 each include a digital to analog converter (D/A), amplifier (A), switch (S) and resistor (R). ADC block 14 includes an analog to digital converter (A/D), amplifier (A), switch (S) and a pair of resistors (R2 and R3). In one embodiment, R2 has a resistance of 2.7M ohms and R3 has a resistance of 100k ohms. The ADC block 14 is used for both impedance measurement and charge measurement. Voltage across the bias resistor R in sink block 16 is amplified and fed into the ADC block 12. The ADC block 12 reads the voltage across the bias resistor, from which the impedance and charge can be calculated. During impedance measurement, signal with constant current applies to all electrodes with respect to one reference electrode (anode), namely, the ground electrode.

When all three switches S are open, the electrode 12 is in high impedance mode. When the switch S in the anode block 18 is closed and the other two switches are open, the electrode 12 is in anode mode. When the switch S in the sink block 16 is closed and the other two switches are open, the electrode 12 is in cathode mode. Switch S in the source block 20 is closed and the other two switches are open to perform active charge balancing for electrode 12.

Each electrode 12 in an electrode array has independent constant current control with respect to the ground electrode. During impedance measurement, different voltages will be applied to different electrodes to achieve the same amount of current for each measured electrode. During charge measurement, the voltage across the bias resistor 15 is substantially continuously read by the ADC block 12, and the data from the ADC transferred to the microcontroller of the IPG. To monitor the charge, both the incoming current and outgoing current will be summed together over time to determine the net residual charge on the electrode using the calculations in the previous paragraph.

The source block 20 is used to perform active charge balance after the stimulation pulse to keep the electrode charge balanced. The sink block 16 is used to generate cathode driven stimulation pulses. The anode block 18 is used to configure the electrode 12 into an anode electrode. As described above, by opening and closing the various switches, the electrode 12 may transition between cathode mode, anode mode, and high impedance mode. The circuit 10 may receive one or more signals, such, for example, (a) SRC_SYNC, a signal to turn on/off the switch S in source block 20; (b) CLK, a clock signal for the D/A converters in the circuit 10; (c) DIN, a digital signal sent to the D/A converters; (d) SNK_SYNC, a signal to turn on/off the switch S in sink block 16; and (e) ANODE_SW, a signal to turn on/off the switch S in anode block 18. VCC is the supplied voltage, typically 16 Volts or 10.5 Volts depending on the design specifications. VCC/2 is the half value of the VCC. MEA_OUT is an output signal from the ADC block 14, which is a measurement signal to calculate the impedance or charge of the electrode.

To substantially continuously monitor the charge density, the sampling rate of determining the charge is at least equal to and preferably greater than the pulse frequency of the stimulation signal. In one embodiment, for a stimulation signal with a pulse width of 500 μs providing 2,000 pulses per second, the sampling rate is at least 2,000 Hz, and preferably twice the pulse frequency (4,000 Hz) or greater. The sampling rate may vary based on the pulse width, wherein signals with shorter pulse widths are preferably subject to higher sampling rates.

In some embodiments, in order to effectively monitor the charge, the minimum current value to be read by the ADC block 14 is preferably less than about 1 mA. Typically, the maximum allowed current for each electrode 12 is about 25 mA. In some embodiments, a minimum measurable current of about 1 mA is sufficient to estimate the charge on the electrode 12. In some embodiments, electrodes with higher or lower minimum measurable current values may be used.

In the event that the microcontroller detects a charge density equal to or greater than the predetermined threshold, it will command the electrodes to be temporarily shorted, i.e., connected to the common ground to discharge. Referring to the exemplary electrode shown in FIG. 2, the microcontroller will switch off the sink block 16 and the source block 20, and switch on the anode block 18. This process typically lasts between a few milliseconds and one second, and the duration of the short can be adjusted by the microcontroller. The optimized duration can be identified by monitoring the frequency of the shorting.

In some embodiments, the charge density is continuously reported by the microcontroller to a technical user interface (TUI), such as a general purpose computer, or a patient user interface (PUI), such as a portable dedicated computing device, running software communicatively coupled to the implanted neurostimulator. In other embodiments, the charge density is reported by the microcontroller only when the charge density equals or exceeds the predetermined threshold. In some embodiments, the clinicians initially use the TUI in a clinical setting with a patient to identify the set of waveforms necessary to generate desired responses from the patient, such as standing, leg flexion, leg extension, blood pressure control, bladder control, etc. Overlapping pulses typically occur when generating multiple simultaneous waveforms with different frequencies that are not harmonically related to each other. Neurostimulation signals are typically repeated in cycles, so, in some embodiments, a clinician may measure charge density for several cycles to determine the pattern of necessary shorts, then deactivate measurement of charge density. For example, if measurement of charge density or waveform overlap indicates that a short is required, the clinician may use the TUI to instruct the microcontroller to enact a short at a predetermined interval during each cycle of neurostimulation. Once the pattern of shorts is established, the microcontroller may cease monitoring charge density to reduce power consumption. Charge density measurement may be reactivated for a limited number of cycles if and when the stimulation configuration is changed to determine whether a different shorting pattern is required.

Residual charge on the electrodes can potentially harm surrounding tissue and cause corrosion to the electrodes. An aspect of the present invention includes detecting residual charge on electrodes after stimulation, and substantially eliminating the charge via shorting the electrodes if the residual charge reaches or exceeds a predetermined threshold. Residual charge refers to charge remaining on an electrode after the charging pulse and discharge pulse, which is sometimes referred to as a recharge pulse, has been applied to the electrodes. Detection of voltage remaining on the electrodes subsequent to the charge and discharge pulses indicates that residual charge exists on one or more of the electrodes. A "k value," a ratio of charge density (Q/A) vs. charge (Q) ratio, is used for distinguishing between stimulation settings which are safe or unsafe for patients and is calculated as follows:

$$\log[(Q/A)=k \cdot \log(Q)]$$

Users may designate a threshold k value, such that a short is enacted if the determined k value exceeds the threshold value. In some embodiments, the threshold value for k is 2.0. In other embodiments, the threshold value is greater than about 1.85 or greater than about 1.7. In further embodiments, the threshold value is greater than or equal to 2.0, greater than or equal to 1.85, or greater than or equal to 1.7. In other embodiments, other threshold values may be designated.

In some embodiments, the charge and charge density are substantially continuously or discontinuously reported to a TUI running software communicatively coupled to the implanted neurostimulator. Using the charge and charge density as inputs, the TUI calculates the k value and alerts the clinician when a possible unsafe set of stimulations will occur. In other embodiments, the charge and charge density are monitored by the microcontroller of the neurostimulator as described above, and the microcontroller calculates the k value. In certain embodiments, the microcontroller detects the charge density and calculates the k value, and the electrodes are temporarily shorted if either the charge density is detected to be equal to or greater than the predetermined threshold or if the k value exceeds a predetermined threshold. In some embodiments, the predetermined threshold for the k value is 1.7, 1.85, or 2.0.

The presence of residual charge on electrodes can be detected by measuring voltage on the electrodes using an ADC, as is generally known in the art. If residual voltage is detected, residual charge is present, which indicates a charge imbalance in the electrodes. Quantifying the amount of residual charge requires an additional step of measuring the impedance of the electrodes, as is typically measured by introducing a voltage difference between two electrodes and then measuring the current through one of them.

In some embodiments, the presence of residual charge on electrodes is detected by measuring voltage and, if the detected voltage reaches or exceeds a predetermined threshold, the electrodes are shorted. In other embodiments, the amount of residual charge on electrodes is calculated by measuring voltage and impedance and, if the calculated residual charge reaches or exceeds a predetermined threshold, the electrodes are shorted. In certain embodiments, shorting the electrodes is enacted by connecting all electrodes in the electrode array to each other and to a common ground to cause the residual charge to dissipate on the electrodes. The microcontroller, or the TUI in other embodiments, can be used to determine time slots between pulses and pass this information to the IPG to use these time slots to measure the residual charge in order not to disturb the stimulation and improve efficiency. These time slots between stimulation pulses may also be used to perform global shorting to reduce the risk of residual charge build up.

Figure 3:
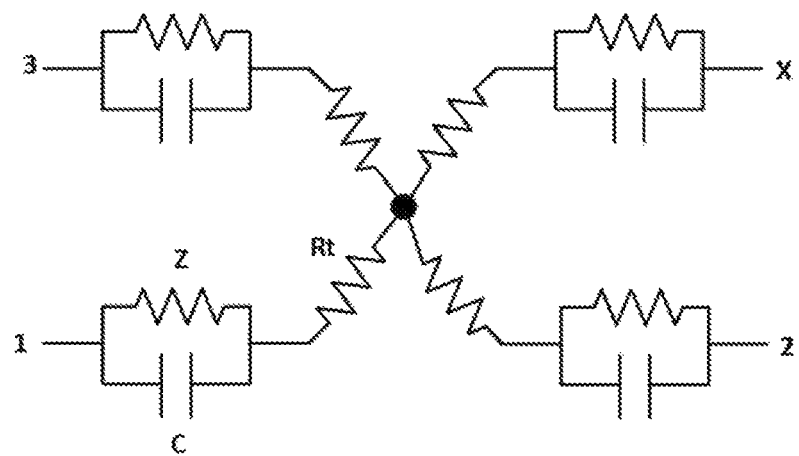
FIG. 3 is a schematic of an exemplary implantable circuit.

Referring now to FIG. 3, an exemplary electrode-tissue interface is comprised of a non-Faradaic element (C), such as a capacitor, in parallel with a Faradaic element (Z), such as a resistor. The non-Faradaic element is preferably electrically reversible such that if the same charge is injected into the metal electrode at (1, 2, 3, X), and is later extracted, the resulting net charge is substantially zero and no residual charge remains. The Faradaic element is preferably not completely electrically reversible, such that injected charge and extracted charge will not result in zero net charge. A charge imbalanced bi-phasic waveform can, at least in theory, deliver a zero net charge. However in practice, repetitive waveforms typically result in a creeping offset over time. Therefore a charge imbalance correction feature is useful to maintain balance and minimize irreversible reactions that may lead to tissue or electrode damage.

In some embodiments, charge balance is corrected by passive discharge wherein electrodes are disconnected and allowed to self-discharge over time. Passive discharge is accomplished by connecting the electrodes to circuit ground in the IPG. Compared to active charge balancing, i.e., shorting, passive discharge typically consumes less power but provides a slower means to dissipate residual charge. This method is particularly suited for correcting charge balance for stimulus waveforms that have defined long periods of no stimulus across all electrodes, as is typically the case when providing neurostimulation for pain management. In other embodiments, charge balance is corrected by active discharge wherein electrodes are shorted together to a common potential or ground to remove charge. This method is particularly suited for correcting charge balance for more complex stimulus waveforms, as overlapping waveforms typically do not produce a consistently periodical spaced time to accomplish the passive discharge method of balance correction.

In one embodiment, charge imbalance is corrected by calculating a k value as described above and enacting a short when the k value reaches or exceeds a predetermined threshold.

In another embodiment, charge imbalance is corrected by detecting voltage as described above and enacting a short when the detected voltage reaches or exceeds a predetermined threshold. The predetermined threshold is preferably greater than zero, as relatively small voltages do not pose a significant risk to equipment or patients.

In a further embodiment, charge imbalance is corrected by detecting voltage and impedance and calculating residual charge as described above and enacting a short when the calculated residual charge reaches or exceeds a predetermined threshold. The predetermined threshold is preferably greater than zero, as relatively small residual charges do not pose a significant risk to equipment or patients.

In a further embodiment, charge imbalance is corrected by calculating charge density as described above and enacting a short when the charge density reaches or exceeds a predetermined threshold.

In another embodiment, charge imbalance is corrected by determining charge as described above and enacting a short when the charge reaches or exceeds a predetermined threshold.

The enacted short is active in some embodiments and passive in other embodiments.

One method of actively measuring electrode charge includes measuring the potential on the metal electrode at (1, 2, 3, X) relative to tissue potential. The potential on the metal electrode can be determined by measuring the potential relative to power supply ground or power supply reference, as is generally known in the art. The tissue potential can be determined by measuring the potential of a reference electrode relative to the power supply ground or power supply reference. The electrode serving as a reference may be an electrode on or near the array that is not configured to perform stimulation, the metal case of the stimulator housing, or an electrode near or part of the metal case.

An exemplary method for measuring the charge for an electrode 1 in a neurostimulator or other implantable device is: (1) measure the potential of electrode 1 relative to one of a power supply ground or a power supply reference, (2) measure the potential of a reference electrode relative to the power supply ground or the power supply reference, and (3) subtract the measured potential of the reference electrode from the measured potential of electrode 1 to determine the potential of electrode 1 relative to the tissue potential.

Multiple reference electrodes may be available in an electrode array including a plurality of electrodes. Therefore multiple measurements can be made using different reference electrodes to compare reference electrode potentials can be made as a test to verify reference function and measure potential drops across tissue resistance (Rt), as shown in FIG. 3. Some stimulation configurations may have multiple electrodes connected to a single source. These configurations are the functional equivalent of a large counter electrode and a small work electrode. The voltage difference between the smaller work electrode and larger counter electrode is the sum of (1) the work electrode to tissue voltage, (2) the voltage across tissue, and (3) the tissue to counter electrode voltage. The ratio of the work electrode to tissue potential and tissue to counter electrode potential is related to the surface areas of the electrodes, with the larger counter electrode having the smaller potential. This measurement approach would be useful in deriving electrode to tissue potential without requiring a tissue reference electrode during the measurement. However to predetermine tissue resistance a separate impedance measurement using a tissue reference measurement may be needed.

Various aspects of different embodiments of the present disclosure are expressed in paragraphs X1 and X2 as follows:

X1. One embodiment of the present disclosure includes a method for controlling neurostimulation charge, comprising determining, for an electrode array including a plurality of electrodes and being configured to produce at least two simultaneous waveforms, at least one of a charge, a charge density, a residual charge, a voltage and a k value on at least one of the plurality of electrodes; and inducing a short in the at least one electrode when the charge, charge density, residual charge, voltage or k value reaches or exceeds a predetermined threshold.

X2. Another embodiment of the present disclosure includes a method for controlling neurostimulation charge, comprising determining, for an electrode array including a plurality of electrodes, at least one of a charge, a charge density, a residual charge, a voltage and a k value on at least one of the plurality of electrodes; and inducing a short in the at least one electrode when the charge, charge density, residual charge, voltage or k value reaches or exceeds a predetermined threshold.

Yet other embodiments include the features described in any of the previous paragraphs X1 or X2, as combined with one or more of the following aspects:

Wherein the electrode array is in electronic communication with a microcontroller, and wherein the determining step is enacted by the microcontroller.

Wherein the determining includes determining the charge and wherein the inducing includes inducing the short in the at least one electrode when the charge reaches or exceeds the predetermined threshold.

Wherein the predetermined threshold is greater than zero.

Wherein the determining includes determining the charge density and wherein the inducing includes inducing the short in the at least one electrode when the charge density reaches or exceeds the predetermined threshold.

Wherein the predetermined threshold is within the range of 80 $\mu C/cm^2$ to 120 $\mu C/cm^2$.

Wherein the predetermined threshold is about 100 $\mu C/cm^2$.

Wherein each waveform has a frequency, and wherein the determining the charge density occurs at a sampling rate, and wherein the sampling rate is greater than the frequency of each of at least two simultaneous waveforms.

Wherein the determining includes determining the residual charge and wherein the inducing includes inducing the short in the at least one electrode when the residual charge reaches or exceeds the predetermined threshold.

Wherein the predetermined threshold is greater than zero.

Wherein the determining includes determining the voltage and wherein the inducing includes inducing the short in the at least one electrode when the voltage reaches or exceeds the predetermined threshold.

Wherein the predetermined threshold is greater than zero.

Wherein the determining includes determining the k value and wherein the inducing includes inducing the short in the at least one electrode when the k-value reaches or exceeds the predetermined threshold.

Wherein the predetermined threshold is within the range of 1.7 to 2.0.

Wherein the predetermined threshold is 1.85.

Wherein each waveform includes at least one pulse, and wherein the inducing does not overlap the at least one pulse.

Wherein the k value is calculated as $\log[(Q/A)=k-\log(Q)]$.

Wherein the short is an active short.

Wherein the short is a passive short.

The foregoing detailed description is given primarily for clearness of understanding and no unnecessary limitations are to be understood therefrom for modifications can be made by those skilled in the art upon reading this disclosure and may be made without departing from the spirit of the invention.

What is claimed is:

1. A method for controlling neurostimulation charge, comprising:

providing, using an electrode array including a plurality of electrodes, at least two simultaneous neurostimulation waveforms, wherein each waveform includes a plurality of pulses;

determining, for the electrode array, at least one of a charge, a charge density, a residual charge, a voltage and a k value on at least one of the plurality of electrodes;

determining at least one time slot between pulses in the plurality of pulses, wherein the at least one time slot does not overlap the pulses; and inducing a short in the at least one electrode during the time slot when the charge, charge density, residual charge, voltage or k value reaches or exceeds a predetermined threshold.

2. The method of claim 1, wherein the determining includes determining the charge and wherein the inducing includes inducing the short in the at least one electrode when the charge reaches or exceeds the predetermined threshold.

3. The method of claim 2, wherein the predetermined threshold is greater than zero.

4. The method of claim 1, wherein the determining includes determining the charge density and wherein the inducing includes inducing the short in the at least one electrode when the charge density reaches or exceeds the predetermined threshold.

5. The method of claim 4, wherein the predetermined threshold is within the range of 80 $\mu C/cm^2$ to 120 $\mu C/cm^2$.

6. The method of claim 5, wherein the predetermined threshold is about 100 $\mu C/cm^2$.

7. The method of claim 4, wherein each waveform has a frequency, and wherein the determining the charge density occurs at a sampling rate, and wherein the sampling rate is greater than the frequency of each of at least two simultaneous waveforms.

8. The method of claim 1, wherein the determining includes determining the residual charge and wherein the inducing includes inducing the short in the at least one electrode when the residual charge reaches or exceeds the predetermined threshold.

9. The method of claim 8, wherein the predetermined threshold is greater than zero.

10. The method of claim 1, wherein the determining includes determining the voltage and wherein the inducing includes inducing the short in the at least one electrode when the voltage reaches or exceeds the predetermined threshold.

11. The method of claim 10, wherein the predetermined threshold is greater than zero.

12. The method of claim 1, wherein the determining includes determining the k value and wherein the inducing includes inducing the short in the at least one electrode when the k-value reaches or exceeds the predetermined threshold.

13. The method of claim 12, wherein the predetermined threshold is within the range of 1.7 to 2.0.

14. The method of claim 13, wherein the predetermined threshold is 1.85.

15. The method of claim 1, wherein the k value is calculated as $\log[(Q/A)=k-\log(Q)]$.

16. The method of claim 1, wherein the short is an active short.

17. The method of claim 1, wherein the short is a passive short.

* * * * *